United States Patent [19]

Yoneda et al.

[11] Patent Number: 5,750,712
[45] Date of Patent: May 12, 1998

[54] 2-(N-CYANOIMINO)-THIAZOLIDIN-4-ONE DERIVATIVES

[76] Inventors: Fumio Yoneda; Mayumi Watanabe; Masatoshi Sakae; Masanori Katsurada; Takaaki Sabato, all of c/o Fujimoto Pharmaceutical Co., Ltd., 3-40, Nishiotuka 1-chome, Matsubara-shi, Osaka 580, Japan

[21] Appl. No.: 493,152

[22] Filed: Jun. 21, 1995

[30] Foreign Application Priority Data

Jul. 29, 1994 [JP] Japan ................................. 6-209067

[51] Int. Cl.[6] ............................................. C07D 277/34
[52] U.S. Cl. .............................................. 548/186; 548/189
[58] Field of Search .................................. 548/189, 186

[56] References Cited

U.S. PATENT DOCUMENTS 5,104,888  4/1992  Yoshioka ................. 514/369
5,143,928  9/1992  Cetenko ................... 514/369

*Primary Examiner*—Robert Gerstl
*Attorney, Agent, or Firm*—Wenderoth, Lind & Ponack

[57] ABSTRACT

A class of novenl compounds represented by the formula (I)

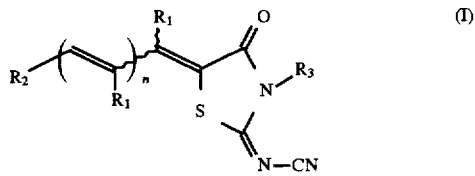

wherein $R_1$s are the same or different groups and each represents hydrogen atom or alkyl group having 1 to 4 carbon atoms; $R_2$ is phenyl group, naphthyl group, or either phenyl or naphthyl substituted with at least one hydroxyl, alkyl having 1 to 4 carbon atoms or alkoxy having 1 to 4 carbon atoms; $R_3$ is hydrogen atom, alkyl group having 1 to 4 carbon atoms or $CH_2COOR_4$ group, in which $R_4$ is hydrogen atom or alkyl group having 1 to 12 carbon atoms; n is 0 or 1, the configuration of 5-methylene group includes both E-isomer and Z-isomer, providing excepting the case wherein $R_1$ is hydrogen or methyl, $R_2$ is 3,5-di-t-butyl-4-hydroxyphenyl, $R_3$ is hydrogen and n is 0 or pharmacologically acceptable salts thereof when $R_3$ or $R_4$ is hydrogen atom The invention also concerns preparation methods thereof. The present comopounds are useful as prophylactic or therapeutic agent for neuropathy, retinopathy, diabetic cataract, impediment in the kidney as tubulo-nephrosis, all known as complications of chronic diabetes and especially aldose reducing enzyme induced complications

9 Claims, No Drawings

2-(N-CYANOIMINO)-THIAZOLIDIN-4-ONE DERIVATIVES

FIELD OF INVENTION

This invention relates to a class of novel compounds, 2-(N-cyanoimino)-thiazolidin-4-one derivatives, represented by the formula (I)

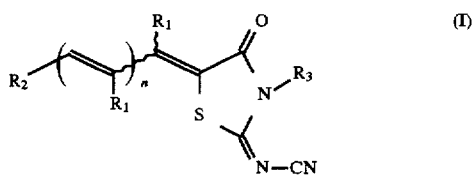
(I)

(wherein $R_1$s are the same or different groups and each represents hydrogen atom or $C_1$-$C_4$ alkyl group; $R_2$ is phenyl group, naphthyl group or either phenyl or naphthyl group substituted with at least one hydroxyl, alkyl having 1 to 4 carbon atoms or alkoxy having 1 to 4 carbon atoms; $R_3$ is hydrogen atom, alkyl group having 1 to 4 carbon atoms or $CH_2COOR_4$ (in which $R_4$ represents hydrogen atom or alkyl having 1 to 12 carbon atoms); n is 0 or 1; and the configuration of 5-methylene group includes both E-isomer and Z-isomer; excepting the case wherein $R_1$ is hydrogen or methyl, $R_2$ is 3,5-di-t-butyl-4-hydroxyphenyl, $R_3$ is hydrogen atom and n is 0) or pharmacologically acceptable salts of the acidic form of said derivatives when $R_3$ or $R_4$ is hydrogen atom.

Examples of alkyl group having 1 to 4 carbon atoms are methyl, ethyl, n-propyl, isopropyl, n-butyl, t-butyl and the like and exsamples of said salts are sodium, potassium, ammonium salt and the like.

BACKGROUND OF THE INVENTION

Various compounds have been proposed for the treatment of diabetes caused by the increase in blood sugar levels which is directly connected with the poor secretion of insulin from the pancreas (hypoglycemic drug).

However, fully satisfactory compounds as medicines for the prophylaxis or treatment of complications of chronic diabetes and inter alia, aldose reducing enzyme induced complications, as, for example, retinopathy, diabetic cataract, neuropathy, atheromic arteriosclerosis and impediment in the kidney or the like, have not been found yet.

Aldose reducing enzyme is an enzyme being capable of reducing an aldose of human or other animal origins, as, for example, glucose or galactose, to the corresponding polyol as, for example, sorbitol or galactitol. When the sorbitol or galactitol thus produced by the action of this enzyme is accumulated into the lenticular, peripheral nerve, kidney or the like of the diabetes or galactosemia patients, there often causes the abovementioned complications (Biochim. Biophys. Acta 15, 8472 (1968); Jap. J. Ophthalmol. 20, 399 (1976); Int. Congr. Ser. Excerpta. Mep. 403, 594 (1944) and Metabolism 28, 456 (1979)).

The present inventors had been working for years on the subject of finding out an effective prophylactic or therapeutic agent for the abovementioned complications of the chronic diabetes, through the impediment of aldose reducing enzyme action. As the result of such studies, the inventors have found a novel class of compounds represented by the formula (I), i.e. 2-(N-cyanoimino)-thiazolidin-4-one derivatives, having an excellent aldose reducing enzyme inhibiting action and succeeded in arriving at the present invention.

Incidentally, in J. Med. Chem. 37,322 (1994), there is described 3,5-di-t-butyl-4-hydroxybenzylidene derivative having a similar construction to those of the present invention and however, they indeed have 5-lipoxygenase and cycloxygenase inhibiting actions, but no aldose reducing enzyme inhibiting action. The present compounds of the formula (I) are novel compounds and they have first been prepared and examined by the inventors. These compounds may be prepared by the reaction of an aldehyde or ketone compound represented by the formula (III)

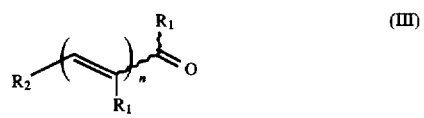
(III)

(wherein $R_1$,$R_2$ and n are as defined hereinbefore) with a 2-(N-cyanoimino) thiazolidin-4-one of the formula (II)

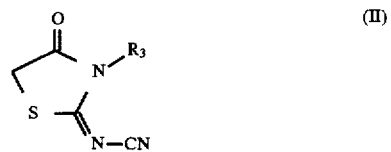
(II)

(in which $R_3$ is as defined hereinbefore) in an appropriate solvent as ethanol, acetonitrile, dioxane, dimethyl formamide, dimethyl sulfoxide, pyridine, toluene, xylene and the like, or without using a solvent, and in the presence of ammonium acetate, at a temperature from room temperature to 200° C., preferably 70°–150° C., for 10 min. to 10 hours, usually 20 min. to 5 hours, under stirring.

Preferably, an excess amount (1.1 to 5 equivalents) of aldehyde or ketone (III) is used as compared with the compound (II). The compound (I) wherein $R_3$ is $CH_2COOR_4$ (in which $R_4$ has the same meaning as defined hereinbefore) may also be prepared by reacting the corresponding $R_3$=H compound in the presence of an alkali or its salt with a halogenized acetic acid or its ester. Examples of said alkali are metal alkali as sodium, potassium or lithium alkali and examples of said salts are sodium, potassium, ammonium salts and the like. There are geometric isomers for the present compounds and however, they are mutually transformable each other in solution by the action of light or heat.

Thus obtained compounds and their salts have an activity for inhibiting the action of aldose reducing enzyme which reduce aldose to the corresponding polyol. This means that the present compounds are useful as prophylactic or therapeutic agents for patients suffering from neuropathy as neuralgia, retinopathy, diabetic cataract, impediment in kidney as tubulo-nephrosis, which are all known as complications specifically connected with the aldose reducing enzyme, among the complications of chronic diabetes as, for example, circulatory disease, impediment in kidney, retinopathy, diabetic cataract, neuropathy, infectious disease and the like.

The invention shall be now more fully explained in the following Examples, which, however, should not be taken as being limitative in any sense to the present invention.

EXAMPLE 1

2-(N-cyanoimino)-5-(2-methyl-3-phenyl propenylidene) thiazolidin-4-one

A mixture of 1.41 g (0.010 mol) of 2-(N-cyanoimino) thiazolidin-4-one, 1.61 g(0.011 mol, 1.1 euqivalent) of alpha-methyl cinnamaldehyde, 0.85 g (0.011 mol, 1.1 equivalents) of ammonium acetate and 30 ml of ethanol was refluxed for 3 hours. After cooling, the mixture was added with ether and the precipitated ammonium salt was suspended in 15 ml of acetone and the suspension was added with 2 ml of conc. hydrogen chloride and 50 ml of water. The precipitated product was filtered. 2.03 g (0.0075 mol) of the objective compound were obtained as yellow needle crystals (yield 75%).

melting point: 202°–203.5° C. (decomp.) (ethanol-DMF)

Mass spectrography 269($M^+$), 254, 201, 174, 169, 141, 115

IR; 3050, 2920, 2760, 2190, 1725, 1590, 1350, 1335, 1310, 1240, 1180 (KBr $cm^{-1}$)

NMR δ=2.21 (3H, s, $CH_3$) 7.34(1H, s, Ph—CH=C) 7.47 (5H, s, aromatic-H) 7.63 (1H, s, CH=C—C=O) (DMSO-d6: ppm)

Elementary analysis: as $C_{14}H_{11}N_3OS$=269.322 Calc. H 4.12%, C 62.44%, N 15.60% Found H 4.26%, C 62.57%, N 15.82%

EXAMPLE 2
2-(N-cyanoimino)-5-(2-methyl-3-phenyl propenylidene)-4-oxo-3-thiazolidine acetic acid A mixture of 1.50 g (0.0049 mol) of potassium salt of 2-(N-cyanoimino)-5-(2-methyl-3-phenyl propenylidene) thiazolidin-4-one, 0.46 g (0.0049 mol) of monochloroacetic acid, 0.81 g (0.049 mol) of potassium iodide and 10 ml of DMF was heated in an oil bath maintained at 60°–70° C. for 1.5 hours. After adding with water, the oily precipitate was separated and purified by means of silica gel chromatography (eluting solvent: hexane: chloroform 3:1) to obtain 0.94 g (0.0029 mol) of the objective compound. Yield 59%, as pale yellow crystals melting point: 174°–175.5° C. (decomp.) (ethyl acetate-ethanol)

Mass spectrography 327($M^+$), 284, 201, 198, 173, 169, 141, 129, 115

IR ; 3300–2250, 2180, 1725, 1570, 1400, 1380, 1325, 1250, 1180, 1100, 740, 695 (KBr $cm^{-1}$)

NMR δ=2.27 (3H, s, $CH_3$) 4.54(2H, s, N—$CH_2$) 7.36 (1H, s, Ph—CH=C), 7.49 (5H, s aromatic-H) 7.85 (1H, s, CH=C—C=O) (DMSO-d6: ppm)

Elementary analysis: as $C_{16}H_{13}N_3O_3S$=327.358 Calc. H 4.00%, C 58.71%, N 12.84% Found H 4.31%, C 58.53%, N 12.73%

EXAMPLE 3
2-(N-cyanoimino)-3-methyl-5-(2-methyl-3-phenylpropenylidene) thiazolidin-4-one A mixture of 2.30 g (0.0080 mol) of ammonium salt of 2-(N-cyanoimino)-5-(2-methyl-3-phenylpropenylidene) thiazolidin-4-one, 0.50 ml (0.0080 mol) of methyl iodide and 20 ml of DMF was stirred at room temperature overnight. After DMF was evaporated, the residue was added with water to precipitate the product. 2.20 g (0.0078 mol) of the objective compound were obtained as pale yellow needle crystals. Yield 97% melting point: 225°–226° C. (decomp.) (ethanol- DMF)

Mass spectrography 283($M^+$), 268, 201, 198, 174, 169, 141, 129, 115

IR; 2200, 1705, 1580, 1430, 1375, 1300, 1125, 765,735, 700 (KBr $cm^{-1}$)

NMR δ=2.32 (3H, s, $CH_3$) 3.31(3H, s, N—$CH_3$) 7.33–7.60 (6H, m, Ph—CH=C,aromatic-H) 7.80 (1H, s, CH=C—C=O) (DMF-d7: ppm)

Elementary analysis: as $C_{15}H_{13}N_3OS$=283.349 Calc. H 4.62%, C 63.58%, N 14.83% Found H 4.87%, C 63.69%, N 14.84%

EXAMPLE 4
2-(N-cyanoimino)-5-(3,4-methylenedioxybenzylidene) thiazolidin-4-one Using the same method as stated in Example 1, 2-(N-cyanoimino)-5-(3,4-methylenedioxybenzylidene) thiazolidin-4-one was prepared from 2-(N-cyanoimino) thiazolidin-4-one and piperonal.

Yield 89%; yellow crystals
melting point: 272° C. (decomp.) (ethanol- DMF)

Mass spectrography 273($M^+$), 178, 148, 120, 94

IR: 3070, 2920, 2760, 2190, 1720, 1580, 1495, 1485, 1445, 1360, 1270, 1230, 1180, 1100, 1035, 920, 485 (KBr $cm^{-1}$)

NMR δ=6.17 (2H, s ,O—$CH_2$—O) 6.95–7.35 (3H, m, 2'-, 5'-, 6'-H) 7.81 (1H, s, CH=C—C=O) (DMSO-d6: ppm)

Elementary analysis: as $C_{12}H_7N_3O_3S$=273.266 Calc. H 2.58%, C 52.74%, N 15.38% Found H 2.55%, C 52.98%, N 15.34%

EXAMPLE 5
2-(N-cyanoimino)-5-(2-naphthylmethylene) thiazolidin-4-one

Using the same method as stated in Example 1, 2-(N-cyanoimino)-5-(2-naphthylmethylene) thiazolidin-4-one was prepared from 2-(N-cyanoimino)thiazolidin-4-one and 2-naphthaldehyde.

Yield 66%; pale yellow crystals
melting point: 243° C. (decomp.) (ethanol- DMF)

Mass spectrography 279($M^+$), 184, 152, 139

IR; 3070, 2930, 2760, 2190, 1720, 1600, 1580, 1480, 1360, 1340, 1330,1300, 1270, 1230, 1210, 1175, 805, 740, 730, 470 (KBr $cm^{-1}$)

NMR δ=7.45–7.87 (3H, m, 3'-,6'-, 7'-H), 7.87–8.35 (5H, m, 1'-,4'-, 5'-,8'-H, CH=C—C=O) (DMSO-d6: ppm)

Elementary analysis: as $C_{15}H_9N_3OS$=279.317 Calc. H 3.25%, C 64.50%, N 15.04% Found H 3.11%, C 64.47%, N 14.91%

EXAMPLE 6
5-benzylidene-2-(N-cyanoimino)-4-oxythiazolidine

Using the same method as stated in Example 1, 5-benzylidene-2-(N-cyanoimino)-thiazolidin-4-one was prepared from 2-(N-cyanoimino) thiazolidin-4-one and benzaldehyde.

Yield 85%; pale yellow crystals
melting point: 226° C. (decomp.) (ethanol- DMF)

Mass spectrography 229($M^+$), 134, 90

IR ; 3030, 2920, 2760, 2220, 1725, 1605, 1490, 1445, 1350, 1290, 1240, 1190, 1180, 525 (KBr $cm^{-1}$)

NMR δ=7.45–7.80 (5H, m, aromatic-H), 7.88(1H,s, CH=C—C=O) (DMSO-d6: ppm)

Elementary analysis: as $C_{11}H_7N_3OS$=229.257 Calc. H 3.32%, C 57.72%, N 18.19% Found H 3.08%, C 57.63%, N 18.33%

EXAMPLE 7
2-(N-cyanoimino)-5-(3-phenylpropenylidene) thiazolidin-4-one

Using the same method as stated in Example 1, 2-(N-cyanoimino)-5-(3-phenylpropenylidene) thiazolidin-4-one was prepared from 2-(N-cyanoimino)thiazolidin-4-one and trans-cinnamaldehyde.

Yield 69%; pale yellow crystals
melting point: 250° C. (decomp.) (ethanol- DMF)

Mass spectrography 255($M^+$), 160, 155, 134, 128, 115

IR ; 3025, 2940, 2750, 2190, 1720, 1595, 1480, 1445, 1400, 1350, 1330,1320, 1260, 1185, 1150, 980, 960, 815, 755, 715 (KBr $cm^{-1}$)

NMR δ=6.89–7.97 (8H, m, CH=CH—CH=C—C=O aromatic-H), (DMSO-d6: ppm)

Elementary analysis: as $C_{13}H_9N_3OS$=255.295 Calc. H 3.55%, C 61.06%, N 16.46% Found H 3.40%, C 61.22%, N 16.34%

EXAMPLE 8
2-(N-cyanoimino)-5-[2-(6-methoxynaphthyl)methylene] thiazolidin-4-one Using the same method as stated in Example 1,2-(N-cyanoimino)-5-[2-(6-methoxynaphthyl)methylene] thiazolidin-4-one was prepared from 2-(N-cyanoimino) thiazolidin-4-one and 6-methoxy- naphtho aldehyde.

Yield 91%; yellow crystals melting point: 256° C. (decomp.) (ethanol- DMF)

Mass spectrography 309($M^+$), 214, 199, 171, 141

IR ; 3050, 2920, 2750, 2190, 1720, 1585, 1490, 1480, 1390, 1350, 1330, 1300, 1270, 1195, 1170, 1035, 860, 840, 800, 710 (KBr $cm^{-1}$)

NMR δ=3.94 (3H, s, O—$CH_3$) 7.25–8.33 (6H, m, aromatic-H), 7.98 (1H, s, CH=C—C=O)(DMSO-d6: ppm)

Elementary analysis: as $C_{16}H_{11}N_3O_2S$=309.343 Calc. H 3.58%, C 62.12%, N 13.58% Found H 3.53%, C 61.89%, N 13.69%

EXAMPLE 9
2-(N-cyanoimino)-5-(1-naphthylmethylene) thiazolidin-4-one

A mixture of 1.79 g (0.010 mol) of potassium salt of 2-(N-cyanoimino) thiazolidin-4-one, 1.72 g (0.011 mol, 1.1 equivalents) of alpha-naphthoaldehyde, 0.85 g (0.011 mol, 1.1 equivalents) of ammonium acetate and 30 ml of ethanol was refluxed for 2 hours. After cooling, the mixture was added with ether to precipitate the potassium salt, which was separated and again suspended in 15 ml of acetone. 2 ml of conc. HCl and 50 ml of water were added to the suspension, and the precipitated crystals were filtered to obtain 2.32 g (0.0083 mol) of the objective compound as yellow crystals. Yield 83%.

Melting point: 230° C. (decomp.) (ethanol- DMF)

Mass spectrography 279($M^+$), 184, 179, 152, 139

IR ; 3120, 3030, 2940, 2770, 2190, 1705, 1600, 1585, 1350, 1215, 795, 770, 720, 550 (KBr $cm^{-1}$)

NMR δ=7.50–7.90 (4H, m, 2'-,3'-,6'-,7'-H) 7.90–8.35 (3H, m, 4'-,5'-,8'-H) 8.54 (1H, s,CH=C—C=O) (DMSO-d6:ppm)

Elementary analysis: as $C_{15}H_9N_3OS$=279.317 Calc. H 3.25%, C 64.50%, N 15.04% Found H 3.64%, C 64.73%, N 15.16%

EXAMPLE 10
2-(N-cyanoimino)-5-(4-hydroxy-3-methoxybenzylidene) thiazolidin-4-one Using the same method as stated in Example 9, 2-(N-cyanoimino)-5-(4-hydroxy-3-methoxybenzylidene) thiazolidin-4-one was prepared from the potassium salt of 2-(N-cyanoimino) thiazolidin-4-one and vanilin.

Yield 91%: yellow orange crystal

Melting point: 238° C. (decomp.) (ethanol- DMF)

Mass spectrography 275($M^+$), 180, 165, 137, 109

IR ; 3330, 3030, 2920, 2760, 2190, 1720(sh), 1695, 1575, 1505, 1370, 1350, 1295, 1220, 1180, 1125, 1020, 810, 720, 620, 530, 480 (KBr $cm^{-1}$)

NMR δ=3.87 (3H, s, O—$CH_3$) 6.80–7.35 (3H, m, aromatic-H), 7.82 (1H, s,CH=C—C=O) (DMSO-d6:ppm)

Elementary analysis: as $C_{12}H_9N_3O_3S$=275.282 Calc. H 3.30%, C 52.36%, N 15.26% Found H 3.52%, C 52.41%, N 15.19%

EXAMPLE 11
2-(N-cyanoimino)-5-(3-methylbenzylidene) thiazolidin-4-one

Using the same method as stated in Example 9, 2-(N-cyanoimino)-5-(3-methylbenzylidene) thiazolidin-4-one was prepared from potassium salt of 2-(N-cyanoimino) thiazolidin-4-one and m-tolualdehyde.

Yield 90%: pale yellow crystal

Melting point: 214°–214.5° C. (decomp.) (ethanol- DMF)

Mass spectrography 243($M^+$), 148, 115

IR ; 3040, 2940, 2760, 2190, 1730, 1610, 1580, 1350, 1295, 1255, 1215, 1160, 780, 720, 540, 520, (KBr $cm^{-1}$)

NMR δ=2.40 (3H, s, $CH_3$) 7.45 (4H, s, aromatic-H), 7.84 (1H, s,CH=C—C=O) (DMSO-d6:ppm)

Elementary analysis: as $C_{12}H_9N_3OS$=243.284 Calc. H 3.73%, C 59.24%, N 17.27% Found H 4.07%, C 59.73%, N 17.49%

EXAMPLE 12
2-(N-cyanoimino)-5-[3-(2- methoxyphenyl) propenylidene] thiazolidin-4-one Using the same method as stated in Example 9, 2-(N-cyanoimino)-5-[3-(2- methoxyphenyl) propenylidene] thiazolidin-4-one was prepared from potassium salt of 2-(N-cyanoimino) thiazolidin-4-one and 2-methoxy cinnamaldehyde.

Yield 80%: yellow orange needle crystal

Melting point: 220° C. (decomp.) (ethanol- DMF)

Mass spectrography 285($M^+$), 201, 190, 185, 175, 147, 131, 115IR; 3160, 3070, 2930, 2750, 2180, 1720, 1580, 1480, 1320, 1240, 1150, 1010, 980, 750, 720 (KBr $cm^{-1}$)

NMR δ=3.90 (3H, s, O—$CH_3$) 6.80–8.00 (7H, m, CH=CH—CH=C—C=O, aromatic-H) (DMSO-d6:ppm)

Elementary analysis: as $C_{14}H_{11}N_3O_2S$=285.321 Calc. H 3.89%, C 58.94%, N 14.73% Found H 4.14%, C 59.09%, N 14.64%

EXAMPLE 13
2-(N-cyanoimino)-5-(1-phenylethylidene) thiazolidin-4-one potassium salt A mixture of 1.41 g (0.010 mol) of 2-(N-cyanoimino) thiazolidin-4-one, 1.80 g(0.015 mol, 1.5 equivalents) of acetophenone, and 0.15 g (0.0020 mol) of ammonium acetate was heated in an oil bath maintained at 110°–120° C. for 20 minutes. After cooling, the mixture was added with 2N HCl and chloroform and an organic layer was separated. Thus obtained organic phase was washed with water, dried and solvent was removed to obtain the crude product, which was then purified by means of silica gel column chromatography (eluting solvent: hexane-chloroform 3:2). The purified product was dissolved in ethanol and added with an equivalent amount of potassium hydroxide and stirred well. Thereafter, ethanol solvent was removed off to obtain the objective potassium salt, which was then recrystallized from isopropanol to obtain the purified product as pale orange crystals.

Melting point: 273°–274° C. (decomp.) (isopropanol)

IR; 2170, 1650, 1580, 1480, 1320, 1290, 1250, 770, 755, 690, 560 (KBr $cm^{-1}$)

NMR δ=2.64 (3H, s, $CH_3$) 7.45 (5H, s, aromatic-H) (DMSO-d6:ppm)

EXAMPLE 14
2-(N-cyanoimino)-5-(1-phenylpropylidene) thiazolidin-4-one

A mixture of 2.82 g (0.020 mol) of 2-(N-cyanoimino) thiazolidin-4-one, 5.36 g (0.040 mol, 2 equivalents) of propiophenone and 1.70 g (0.022 mol) of ammonium acetate was heated in a bath maintained at 130°–140° C. for 25 minutes. After cooling, the mixture was added with 2N NaOH and ether and mixed well. The aqueous phase was separated, acidified with conc. HCl and extracted with chloroform. The chloroform extract was then washed with water, dried and the solvent was removed off to obtain the crude product. The crude product was thereafter subjected to silica gel column chromatography (eluting solvent :hexane-chloroform 3:2) to obtain 1.52 g ( 0.0059 mole) of the objective compound.

Yield: 30% as pale yellow crystals

Melting point: 191°–192° C. (decomp.) (ethyl acetate-hexane)

Mass spectrography 257($M^+$), 190, 162, 157, 147, 129, 103

IR ;3030, 2920, 2760, 2180, 1710, 1590, 1480, 1330, 1210, 1035, 770, 695, 550 (KBr $cm^{-1}$)

NMR δ=0.98 (3H, t, J=7.5 Hz $CH_3$) 3.25 (2H, q, J=7.5 Hz, $CH_2$) 7.45 (5H,s, aromatic-H) (DMSO-d6:ppm)

Elementary analysis: as $C_{13}H_{11}N_3OS$=257.311 Calc. H 4.31%, C 60.68%, N 16.33% Found H 4.49%, C 60.44%, N 16.10%

EXAMPLE 15

2-(N-cyanoimino)-5-[1-(2-naphthyl)ethylidene] thiazolidin-4-one

A mixture of 1.41 g (0.010 mol) of 2-(N-cyanoimino) thiazolidin-4-one, 2.55 g (0.015 mol, 1.5 equivalents) of acetonaphthone and 0.15 g (0.0020 mol) of ammonium acetate was heated in an oil bath maintained at 120°–125° C. for 20 minutes. After cooling, the mixture was added with 2N HCl and chloroform and an organic phase was separated, washed with water, dried and distilled the solvent off. Thus obtained crude product was purified by means of silica gel column chromatography (eluting solvent: hexane-chloroform 3:2) to obtain 1.76 g ( 0.0060 mol) of the purified objective compound.

Yield: 60% as pale yellow crystals

Melting point: 191°–191.5° C. (decomp.) (ethyl acetate-hexane)

Mass spectrography 293($M^+$), 198, 165, 128

IR ;3120, 3050.2940, 2770, 2180, 1720(sh), 1700, 1580, 1330, 1230, 1025, 825, 750, 720, 635, 540, 480 (KBr $cm^{-1}$)

NMR δ=2.81 (3H, s, $CH_3$) 7.50–7.85 (3H, m, 3'-, 6'-, 7'-H) 7.85–8.25 (4H, m, 1'-, 4'-, 5'-, 8'-H) (DMSO-d6:ppm)

Elementary analysis: as $C_{16}H_{11}N_3OS$=293.344 Calc. H 3.78%, C 65.51%, N 14.33% Found H 4.02%, C 65.39%, N 13.89%

EFFECT OF THE INVENTION

Aldose reducing enzyme inhibiting activity of the respective 2-(N-cyanoimino) thiazolidin-4-one derivatives was measured according to the method by Hayman et al (J. Biol. Chem., 240 877 (1965)) The employed aldose reducing enzyme was Human, Recombinant.

The following table shows "inhibition rate (%)" which means the inhibiting activity at the $1.0\times10^{-7}$ mol concentration level of the tested compound.

TABLE 1

| Example No. | Inhibition rate (%) |
| --- | --- |
| 1 | 72 |
| 2 | 100 |
| 3 | 12 |

TABLE 1-continued

| Example No. | Inhibition rate (%) |
| --- | --- |
| 4 | 44 |
| 5 | 44 |
| 6 | 32 |
| 7 | 44 |
| 8 | 68 |
| 9 | 20 |
| 10 | 100 |
| 11 | 52 |
| 12 | 84 |
| 13 | 60 |
| 14 | 12 |
| 15 | 64 |

What is claimed is:

1. 2-(N-cyanoimino)-thiazolidin-4-one compounds of the formula(I):

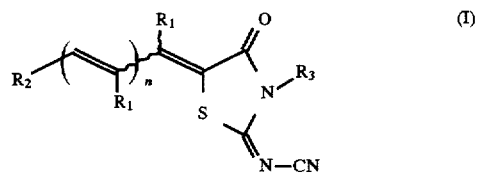

wherein $R_1$s are the same or different and each represents hydrogen or alkyl having 1 to 4 carbon atoms; $R_2$ is phenyl, naphthyl or either phenyl or naphthyl substituted with at least one hydroxyl, alkyl having 1 to 4 carbon atoms or alkoxy having 1 to 4 carbon atoms; $R_3$ is hydrogen alkyl having 1 to 4 carbon atoms or $CH_2COOR_4$ in which $R_4$ is hydrogen or alkyl having 1 to 12 carbon atoms; n is 0 or 1 and the configuration of 5-methylene group includes both E-isomer and Z-isomer, excepting the case wherein $R_1$ is hydrogen or methyl, $R_2$ is 3,5-di-t-butyl-4-hydroxyphenyl, $R_3$ is hydrogen and n is 0 or pharmacologically acceptable salts of the acidic form of said compounds when $R_3$ or $R_4$ is hydrogen.

2. A process for preparing a 2-(N-cyanoimino)-thiazolidin-4-one compounds represented by the formula (I)

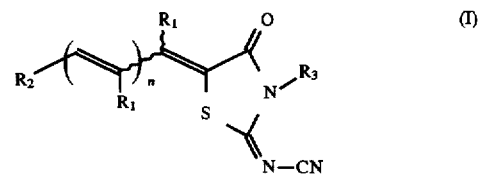

wherein $R_1$, $R_2$, n and $R_3$ are as defined hereunder or salts thereof, which comprises reacting a 2-(N-cyanoimino)-thiazolidin-4-one of the formula (II)

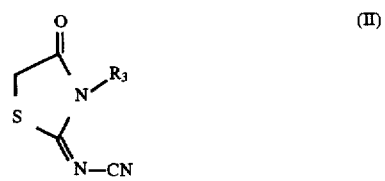

in which $R_3$ is hydrogen, alkyl having 1 to 4 carbon atoms or $CH_2COOR_4$, and $R_4$ is hydrogen or alkyl having 1 to 12 carbon atoms or its salt with an aldehyde or ketone of the formula (III)

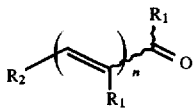 (III)

in which $R_1$s are the same or different and each represents hydrogen or alkyl having 1 to 4 carbon atoms; $R_2$ is phenyl, naphthyl, or either phenyl or naphthyl substituted with at least one hydroxyl, alkyl having 1 to 4 carbon atoms or alkoxy having 1 to 4 carbon atoms; n is 0 or 1; excepting the case wherein $R_1$ is hydrogen or methyl, $R_2$ is 3,5-di-t-butyl-4-hydroxyphenyl and n is 0.

3. 2-(N-cyanoimino)-5-(2-methyl-3-phenyl propenylidene)-thiazolidin-4-one.

4. 2-(N-cyanoimino)-5-(2-methyl-3-phenyl propenylidene)-4-oxo-3-thiazolidine acetic acid.

5. 2-(N-cyanoimino)-5-[2-(6-methoxy naphthyl) methylene]-thiazolidin-4-one.

6. 2-(N-cyanoimino)-5-(4-hydroxy-3-methoxy benzylidene)-thiazolidin-4-one.

7. 2-(N-cyanoimino)-5-[3-(2-methoxyphenyl) propenylidene]-thiazolidin-4-one.

8. 2-(N-cyanoimino)-5-(1-phenylethylidene)-thiazolidin-4-one potassium salt.

9. 2-(N-cyanoimino)-5-[1-(2-naphthyl) ethylidene]-thiazolidin4-one.

* * * * *